United States Patent
Oleszkiewicz et al.

(10) Patent No.: US 7,993,531 B2
(45) Date of Patent: Aug. 9, 2011

(54) BIOLOGICAL FLUID FILTRATION SYSTEMS AND METHODS

(75) Inventors: Anthony Oleszkiewicz, Round Lake, IL (US); Bryan Blickhan, Zion, IL (US); Mark B. Jones, Libertyville, IL (US)

(73) Assignee: Fenwal, Inc., Lake Zurich, IL (US)

( * ) Notice: Subject to any disclaimer, the term of this patent is extended or adjusted under 35 U.S.C. 154(b) by 386 days.

(21) Appl. No.: 12/098,876

(22) Filed: Apr. 7, 2008

(65) Prior Publication Data

US 2008/0251459 A1 Oct. 16, 2008

Related U.S. Application Data

(60) Provisional application No. 60/910,566, filed on Apr. 6, 2007.

(51) Int. Cl.
*B01D 37/00* (2006.01)
*B01D 29/00* (2006.01)

(52) U.S. Cl. ........ 210/767; 210/645; 210/800; 210/120; 210/188; 210/252; 210/254; 210/257.1; 210/435; 210/436; 210/472; 604/28; 604/403; 604/405; 604/406; 604/408

(58) Field of Classification Search .......... 210/644, 210/645, 767, 120, 188, 252, 254, 257.1, 210/435, 436, 472, 800; 95/241; 96/155; 604/403, 405, 406, 408, 28
See application file for complete search history.

(56) References Cited

U.S. PATENT DOCUMENTS

| | | | |
|---|---|---|---|
| 4,284,209 A | 8/1981 | Barbour, Jr. |
| 4,753,739 A | 6/1988 | Noble |
| 4,838,872 A | 6/1989 | Sherlock |
| 4,892,668 A | 1/1990 | Harmony et al. |
| 5,100,564 A | 3/1992 | Pall et al. |
| 5,543,062 A | 8/1996 | Nishimura |
| 5,632,906 A | 5/1997 | Ishida et al. |
| 5,690,815 A | 11/1997 | Krasnoff et al. |
| 5,863,436 A | 1/1999 | Matkovich |
| 6,053,885 A | 4/2000 | Beshel |
| 6,171,493 B1 | 1/2001 | Zia et al. |

(Continued)

FOREIGN PATENT DOCUMENTS

DE 19537271 A1 4/1997

(Continued)

OTHER PUBLICATIONS

International Search Report and Written Opinion for Application No. PCT/US2008/059558, dated Sep. 26, 2008.

(Continued)

*Primary Examiner* — John Kim
(74) *Attorney, Agent, or Firm* — Cook Alex Ltd.

(57) ABSTRACT

Biological fluid filtration methods are provided for the treatment of gas within a biological fluid filtration system. A quantity of biological fluid is flowed under the force of gravity through a leukocyte removal filter and into a post-filter container. The post-filter container has a maximum vented volume that is approximately the same as the quantity of biological fluid flowed through the filter and into the post-filter container. At least a substantial portion of the gas in the post-filter container is vented therefrom without separately restricting expansion of the post-filter container and without manually manipulating the post-filter container to expel gas.

8 Claims, 8 Drawing Sheets

U.S. PATENT DOCUMENTS

| | | |
|---|---|---|
| 6,358,420 B2 | 3/2002 | Blickhan et al. |
| 2003/0004453 A1 | 1/2003 | Goudaliez et al. |
| 2003/0104349 A1* | 6/2003 | Bischof et al. .................. 435/2 |
| 2008/0156728 A1* | 7/2008 | Blickhan et al. .............. 210/645 |

FOREIGN PATENT DOCUMENTS

| | | |
|---|---|---|
| EP | 1048305 A | 11/2000 |
| EP | 1938850 A1 | 7/2008 |
| WO | WO 96/39940 A1 | 12/1996 |
| WO | WO 02/11855 A1 | 2/2002 |

OTHER PUBLICATIONS

European Search Report and Abstract for Application No. 07025194.7-2310, May 20, 2008.

* cited by examiner

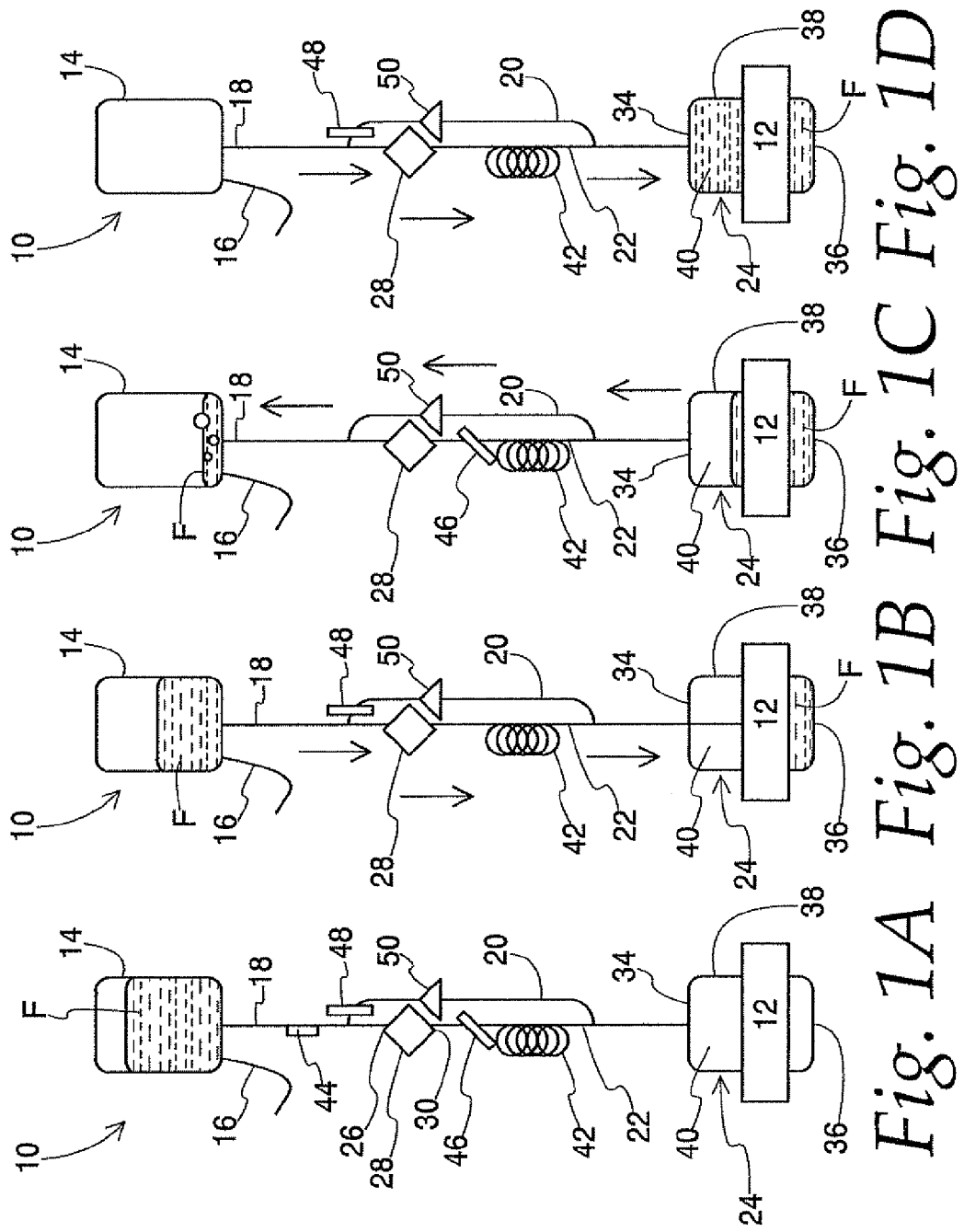

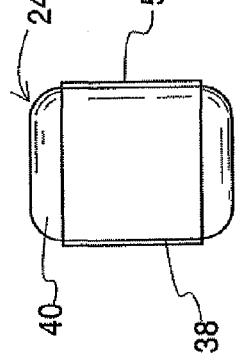
Fig. 7A
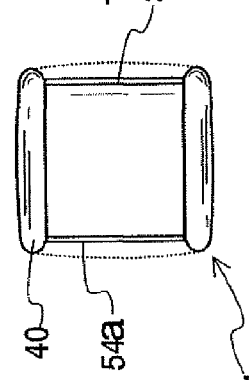
Fig. 7B
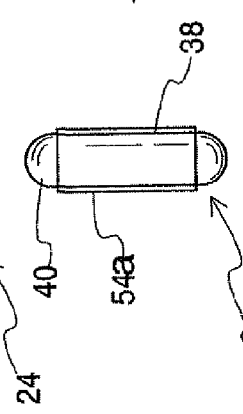
Fig. 7C
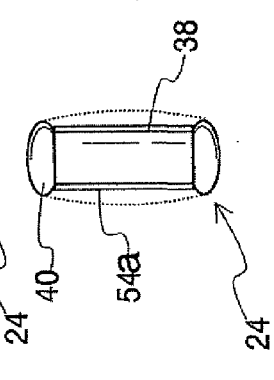
Fig. 7D
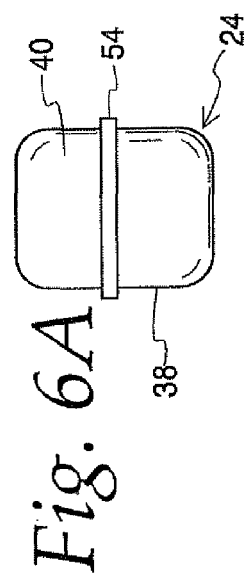
Fig. 6A
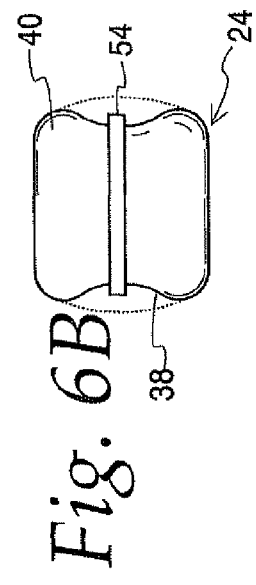
Fig. 6B
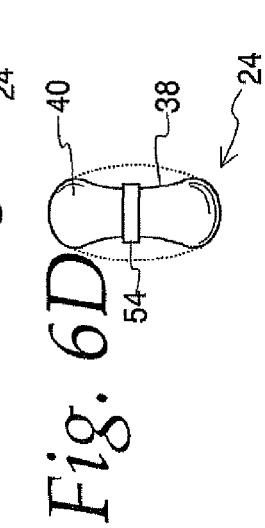
Fig. 6C
Fig. 6D

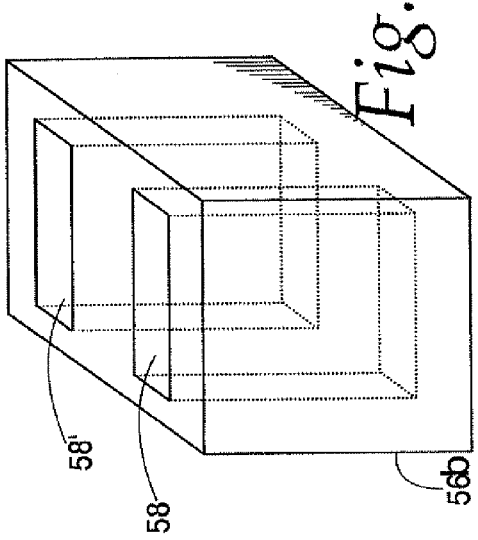
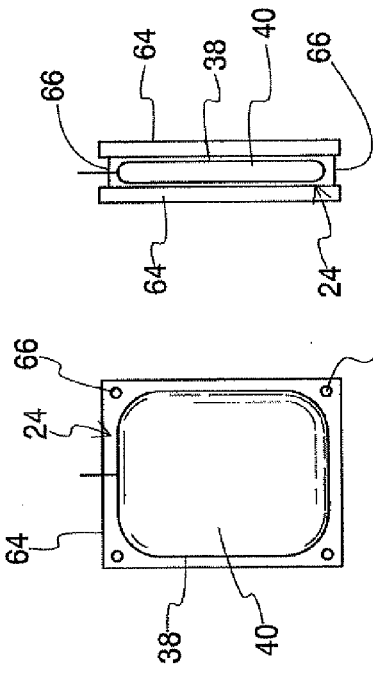
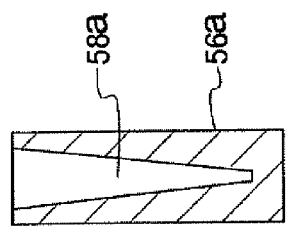
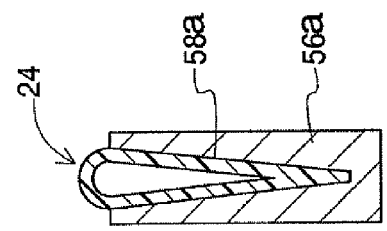
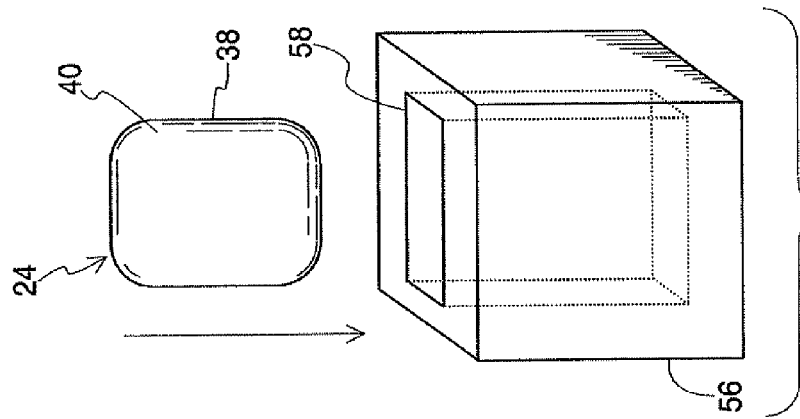

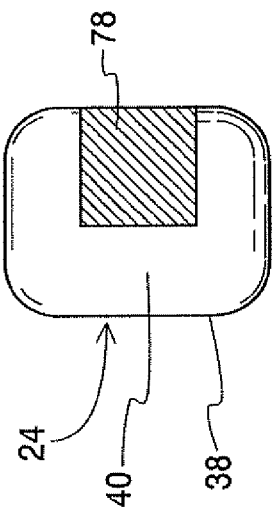
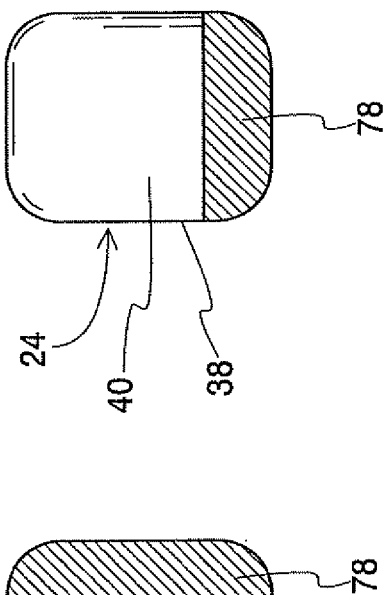
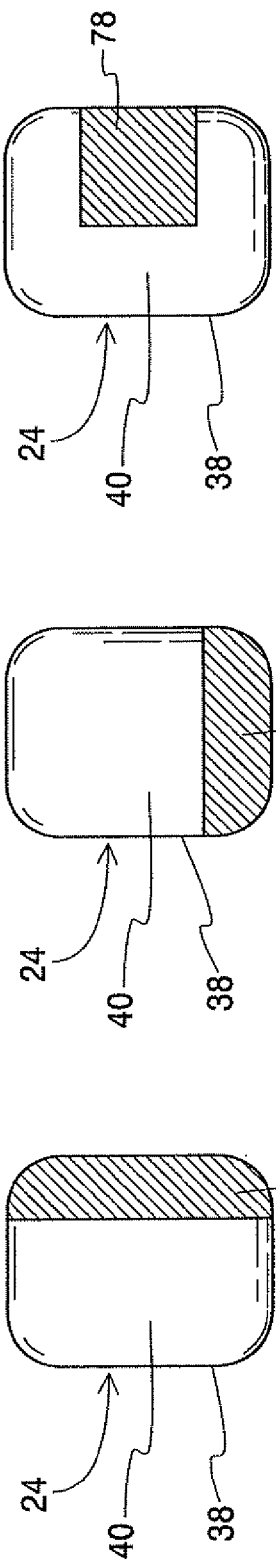
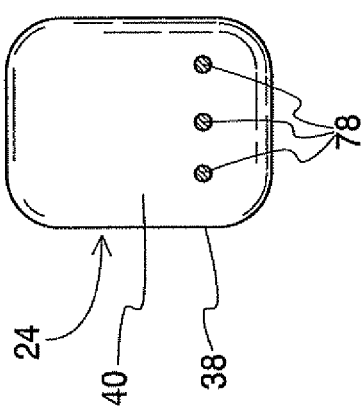
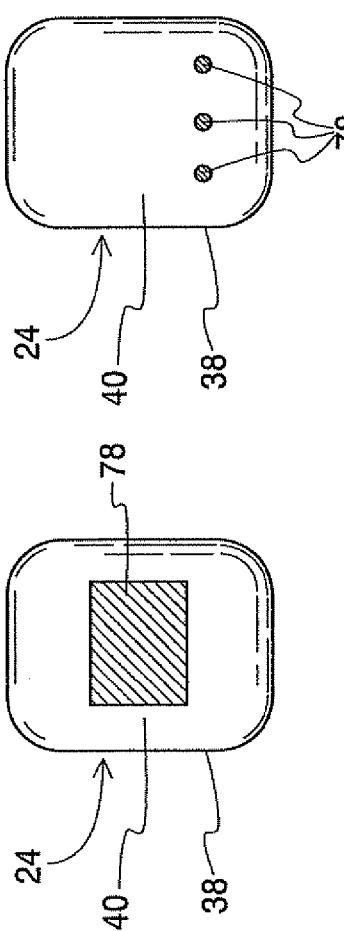

BIOLOGICAL FLUID FILTRATION SYSTEMS AND METHODS

CROSS REFERENCE TO RELATED APPLICATIONS

This application claims priority from and the benefit of provisional patent application Ser. No. 60/910,566, filed Apr. 6, 2007, which is hereby incorporated herein by reference.

BACKGROUND

1. Field of the Disclosure

This disclosure generally relates to apparatus and methods for filtering a biological fluid, such as (but not limited to) the removal of leukocytes from whole blood or a blood component. More particularly, the disclosure relates to apparatus and methods for removing air from a fluid container having an amount of filtered fluid.

2. Description of Related Art

Prior to transfusion of blood or a blood component into a recipient, it is common to filter the blood to remove leukocytes. This process is commonly referred to as leukoreduction. It may be desirable to remove leukocytes from blood or a blood component prior to transfusion because they can trigger a broad range of adverse reactions in a recipient, ranging from minor effects, such as chills, to more serious effects, such as the transmission of cytomegalovirus, which can be fatal to recipients with weakened immune systems.

Commonly, leukoreduction involves the transfer of blood or a blood component from a pre-filter fluid container to a post-filter fluid container through a tubing line having a leukoreduction filter. The filter typically includes a quantity of air that is pushed out of the filter upon priming the same during a filtration application. It is desired to prevent this air from moving into the post-filter container and remaining there, because such air aggregation can prevent complete filtration of the blood, as will be described in greater detail herein, and decrease the quality and storability of the filtered blood. Even when the blood or blood component is used a short time after filtration, there is a general preference among users to have as little air in the post-filter container as possible.

Known approaches to air management include filtration systems that are vented to the atmosphere or a gas container and those incorporating a bypass line. For example, U.S. Pat. No. 5,863,436 to Matkovich, which is hereby incorporated herein by reference, describes several leukoreduction systems incorporating one or more air vents. One commercial system according to the description of Matkovich is the Pall SAVE™ system, which is incorporated into the Leukotrap® WB Filtration System from Pall Corporation of Glen Cove, N.Y. The Leukotrap® WB Filtration System comprises a pre-filter container connected to a post-filter container by a filter line having a leukoreduction filter. A pre-filter air vent is associated with the filter line between the pre-filter container and the filter, while a post-filter air vent is associated with the filter line between the filter and the post-filter container. In use, the pre-filter container is hung above the post-filter container and a cannula of the pre-filter container is broken to allow fluid flow into the filter line. The fluid is prevented from flowing into the pre-filter air vent by a removable cap, so it instead flows into the filter. The filter is allowed to prime, with air exiting the system through the post-filter air vent. When the filter is fully primed, a cannula between the post-filter vent and the post-filter container is broken to allow fluid and air to flow into the post-filter container. Due to pressure differentials in the system, the filtration process ceases prior to complete filtration of all the fluid, i.e., with an amount of fluid remaining in the filter. At that time, the cap on the pre-filter air vent is removed to allow a gas to enter the filter line and purge any remaining fluid from the inlet side of the filter.

One problem with systems according to the foregoing description is that no means are provided to remove air from the post-filter container, either during or after filtration. While the post-filter vent removes the air that is purged from the filter, gas may be initially present in the system at other locations, such as in the containers or the tubing, as a result of the manufacturing process. This gas is pushed into the post-filter container during filtration and can lead to the aforementioned diminished performance and quality concerns if not removed during or after filtration.

In response to the foregoing problem, leukoreduction systems incorporating bypass lines allow removal of air and other gases from the post-filter container during and/or after filtration. Several examples of known leukoreduction systems with bypass lines are described in U.S. Pat. No. 6,358,420 to Blickhan et al., which is hereby incorporated herein by reference. In one system, a pre-filter container is connected to a post-filter container by a filter line having a leukoreduction filter. Tubing comprising a bypass line is connected to the filter line at opposite sides of the filter, thereby allowing for fluid communication between the containers along a path that bypasses the filter. The bypass line is provided with a one-way valve, typically a check valve, which only allows air and fluid flow toward the pre-filter container from the post-filter container. In use, the pre-filter container is hung above the post-filter container and a cannula of the pre-filter container is broken to allow fluid flow into the filter line. The fluid is prevented from flowing through the bypass line and into the post-filter container by the one-way valve. The fluid flows through the filter and into the post-filter container, along with an amount of air. Due to pressure differentials in the system, the filtration process ceases prior to complete filtration of the fluid, i.e., with an amount of fluid remaining in the filter. At that time, a slide clamp is placed on the filter line, between the filter and the post-filter container, and the post-filter container is squeezed to force air through the bypass line and toward the pre-filter container. Squeezing the post-filter container to remove air and other gases is sometimes referred to as "burping" the container. When the post-filter container has been "burped," the clamp is removed from the filter line and the filter is allowed to more completely drain.

According to another leukoreduction system described in Blickhan et al., one end of the bypass line is connected to the filter line at a position between the pre-filter container and the filter, while the other end is connected directly to the post-filter container. This system operates similarly to the previously described system of Blickhan et al. to filter blood or a blood component and remove air from the post-filter container.

While systems incorporating bypass lines represent improvements over the systems of Matkovich in terms of air removal from the post-filter container, the need to manually "burp" the container to remove air may be problematic. In particular, the amount of air removal is directly dependent on the skill of the user, which can potentially lead to insufficient or incomplete air removal.

A more recent approach to eliminating the manual "burping" step is to allow for automatic "burping" of the post-filter container. Several such systems are described in U.S. Pat. No. 6,171,493 to Zia et al., which is hereby incorporated herein by reference. Rather than connecting the bypass line to one or more sections of the filter line, one end of the bypass line is directly connected to the pre-filter container and the other end of the bypass line is directly connected to the post-filter container. The pre-filter container is hung above the post-filter container and, in one embodiment, a loop portion of the filter line is elevated above the fluid level in the pre-filter container to prevent fluid from flowing through the bypass line and into the post-filter container. A clamp on the filter line is opened to allow fluid flow through the filter line and the filter. Air in the filter is pushed into the post-filter container by the blood and begins to accumulate therein and/or to leak from the post-filter container into the bypass line. When the pressure in the post-filter container reaches a sufficient level and the pressure in the pre-filter container decreases sufficiently (typically to a vacuum state), some of the air moves up the bypass line, through the loop portion, and into the pre-filter container. The return of air to the pre-filter container increases the pressure above the filter and assists in more completely draining any remaining fluid from the filter.

In theory, the "burping" system of Zia et al. improves on previously known systems by automatically removing air from the post-filter container, without requiring a manual "burping" operation. However, the efficiency of the Zia et al. system is contingent on the pressure differential between the post-filter container and the pre-filter container. Optimal filtration results are achieved when pressure in the post-filter container is maximized. If only a small amount of fluid is to be filtered, then the post-filter container will remain relatively empty and the pressure developed therein will not be sufficient to re-circulate the air to the pre-filter container. In such situations, the post-filter container must be manually squeezed to remove air, thereby representing a failure of the intended automatic "burping" feature.

Therefore, there remains a need for apparatus and methods for more efficiently removing air from a post-filter container, especially during filtration of a smaller amount of fluid.

SUMMARY

There are several aspects of the present invention which are embodied together or separately in the devices, systems and methods described and claimed below.

In one aspect, a method of filtering leukocytes from a quantity of biological fluid comprises flowing a quantity of biological fluid under the force of gravity through a leukocyte removal filter and into a post-filter container. The post-filter containver has a maximum vented volume that is approximately the same as the quantity of biological fluid flowed through the filter and into the post-filter container. At least a substantial portion of any gas in the post-filter container is vented therefrom without separately restricting expansion of the post-filter container and without manually manipulating the post-filter container to expel gas.

Filtration systems and methods generally described herein are particularly well-suited for use in connection with leuko-reduction of blood or a blood component. However, filtration systems and methods according to the present invention are not limited to use with specific fluids or filtration processes and may be applied to virtually any biological fluid treatment system involving filtration between two containers.

BRIEF DESCRIPTION OF THE DRAWINGS

FIGS. 1A-1D are schematic views of a filtration system according to the present invention and a method of using the same;

FIG. 6A is a front elevational view of a post-filter container having a volume restriction provided as a restrictor member, with the container in an unexpanded or pre-filtration condition;

FIG. 6B is a front elevational view of the post-filter container and restrictor member of FIG. 6A, with the container in a restricted maximum volume condition;

FIG. 6C is a side elevational view of the post-filter container and restrictor member of FIG. 6A, with the container in an unexpanded or pre-filtration condition;

FIG. 6D is a side elevational view of the post-filter container and restrictor member of FIG. 6A, with the container in a restricted maximum volume condition;

FIG. 7A is a front elevational view of a post-filter container having an alternative restrictor member, with the container in an unexpanded or pre-filtration condition;

FIG. 7B is a front elevational view of the post-filter container and restrictor member of FIG. 7A, with the container in a restricted maximum volume condition;

FIG. 7C is a side elevational view of the post-filter container and restrictor member of FIG. 7A, with the container in an unexpanded or pre-filtration condition;

FIG. 7D is a side elevational view of the post-filter container and restrictor member of FIG. 7A, with the container in a restricted maximum volume condition;

FIG. 8A is a front perspective view of a post-filter container and a volume restriction provided as a housing;

FIG. 8B is a side cross-sectional view of a housing having a "wedge-shaped" cavity;

FIG. 8C is a side cross-sectional view of the housing of FIG. 8B, with a post-filter container partially received within the cavity;

FIG. 8D is a front perspective view of a housing having a plurality of container-receiving cavities;

FIG. 9A is a front elevational view of a post-filter container having a volume restriction provided as first and second plates;

FIG. 9B is a side elevational view of the post-filter container and plates of FIG. 9A;

FIGS. 13A-13D are front elevational views of various post-filter containers having a volume restriction provided as an internal bond;

FIG. 14 is a front elevational view of a post-filter container having a volume restriction provided as a plurality of internal bonds.

DESCRIPTION OF THE PREFERRED EMBODIMENTS

Figure 5:
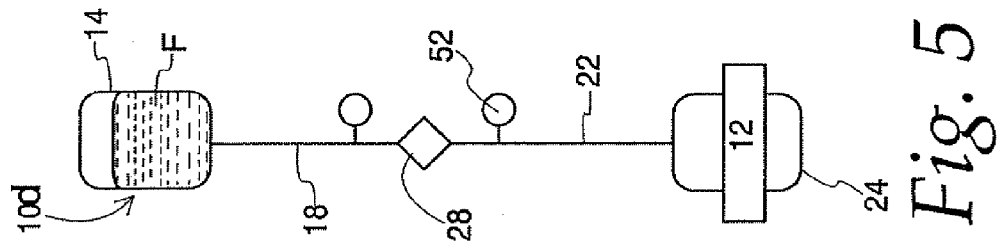
FIGS. 2-5 are schematic views of other filtration systems incorporating a volume restriction.

The embodiments disclosed herein are for the purpose of providing the required description of the present invention.

These embodiment, however, are exemplary of the invention, which may be embodied in various forms. Therefore, specific details disclosed herein are not to be interpreted as limiting the invention as defined in the accompanying claims.

FIGS. 1A-1D illustrate a filtration system, generally indicated at 10, suitable for use in combination with a volume restriction 12 (shown schematically in FIGS. 1A-1D) of the present invention. Other suitable filtration systems 10a, 10b, 10c, and 10d are illustrated in FIGS. 2-5, respectively, although it will be appreciated from the following description that the volume restriction 12 may be used with a wide range of filtration systems, including those systems comprising a component of a larger fluid processing set, and the present invention is not limited to the illustrated systems. It may be advantageous to practice the subject matter described herein with an integral, pre-assembled fluid flow system, although the apparatus and methods described herein may also be employed as part of a fluid flow system that originates as separate components and is assembled at the point of use.

The filtration system 10 of FIGS. 1A-1D includes a pre-filter container 14 adapted to contain a biological fluid "F." As used herein, the term "biological fluid" refers to any bodily fluid that may contain leukocytes, including without limitation whole blood or a separated blood component, whether alone or in combination with other fluids, such as anticoagulant or a storage solution. The pre-filter container 14 may include a needle and associated tubing 16 for drawing an amount of fluid into the container 14, although any method of filling the pre-filter container 14 may be used without departing from the scope of the present invention. A pre-assembled filtration system that includes a pre-filter container and associated tubing and needle in which the needle is the only open access into the system is commonly referred to as a "closed" system. However, the subject matter disclosed herein is not limited to a closed system. For example, in another embodiment, the pre-filter container 14 may be provided separately from the remainder of the filtration system 10 to be filled with a biological fluid "F" from a source prior to associating the pre-filter container 14 with the system. According to known design, the pre-filter container 14 may be comprised of a flexible, transparent material, such as polyvinyl chloride or other medical grade plastic.

Figure 4:
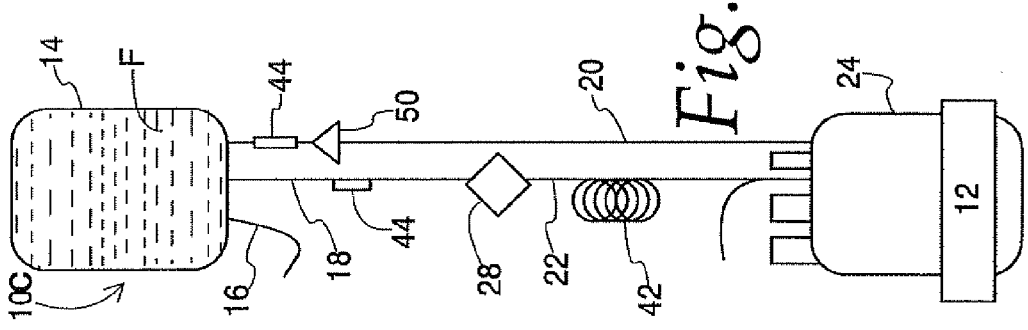

The pre-filter container 14 includes at least one outlet port with an associated length of tubing, referred to herein as a filter inlet flow path 18. The pre-filter container 14 may include other ports connectable by tubing to various peripheral devices, including other fluid containers. In some systems, such as the filtration systems 10a and 10c of FIGS. 2 and 4, one of the ports is associated with a bypass line 20 directly or indirectly connectable to a filter outlet flow path 22 (FIG. 2) or a post-filter container 24 (FIG. 4). These configurations and features will be described in greater detail herein. The exact structure of the pre-filter container 14 is not intended to limit the scope of the present invention and may vary from the particular structures described and illustrated herein.

The filter inlet flow path 18 is preferably connected to a bottom portion of the pre-filter container 14 to allow for fluid flow therethrough preferably by gravity. The other end of the filter inlet flow path 18 is connected to a filter inlet 26 of a filter 28. As will be described in greater detail herein, the biological fluid "F" flows downward from the pre-filter container 14, through the filter inlet flow path 18, and into the filter inlet 26 under the force of gravity. Accordingly, to ensure that the biological fluid "F" has developed sufficient pressure to pass through the filter 28, the pre-filter container 14 is hung a selected height above the filter 28. For example, in one embodiment, the pre-filter container 14 may be positioned approximately 18-24 inches above the filter 28.

The filter 28 further includes a filter outlet 30, which is connected to an inlet port of an expandable post-filter container 24 by a length of tubing, referred to herein as a filter outlet flow path 22. The filter inlet flow path 18 and the filter outlet flow path 22 are collectively referred to herein as a filter line. A suitable filter media (not shown) is located within the filter so that fluid passing from the filter inlet flow path 18 to the filter outlet flow path 22 is suitably filtered. The exact structure and function of the filter 28 is not intended to limit the scope of the present invention, but a leukoreduction filter is suitable for use in combination with a biological fluid "F" comprising blood or a blood component. For example, the leukoreduction filters in the Sepacell® line from Asahi Kasei Medical Co., Ltd. of Tokyo, Japan are suitable for use with filtration systems according to the present invention.

The post-filter container 24 is adapted to contain a filtered biological fluid "F" and is comprised of a flexible, preferably transparent material, such as polyvinyl chloride or other medical grade plastic. The post-filter container 24 may be comprised of one or more flexible sheets to define a top end 34, a bottom end 36, and a sidewall 38 extending therebetween. The sidewall 38 defines an interior volume or portion 40 that is expandable because of, for example, stretching of the plastic from a minimum volume to a maximum volume by receipt of fluid "F." During storage, transport, and before filtration has commenced (FIG. 1A), the post-filter container 24 is substantially flat and at or near the minimum volume, typically with a nominal amount of air contained therein as a result of the manufacturing process. As the post-filter container 24 is filled with an increasing amount of fluid "F," it will continually expand and increase in volume, up to the unrestricted maximum volume in which the post-filter container 24 generally resembles a pillow or teardrop.

The post-filter container 24 may include a plurality of ports (FIGS. 2-4) connectable by tubing to various peripheral devices, including other fluid containers. In some systems, such as the filtration systems 10b and 10c of FIGS. 3 and 4, one of the ports is associated with a bypass line 20 connectable to the filter inlet flow path 18 (FIG. 3) or the pre-filter container 14 (FIG. 4).

In accordance with the present invention, the post-filter container 24 also includes a volume restriction, schematically illustrated in FIGS. 1A-5 and generally identified as element 12. The volume restriction 12 may take any of a number of forms, as will be described in greater detail herein, and serves the purpose of limiting the volumetric expansion of the post-filter container 24 upon receipt of a fluid. As per the foregoing description, the efficiency of two-bag filtration systems increases as the filled volume of the post-filter container (i.e., the amount of fluid "F" received by the post-filter container 24) approaches the maximum expanded volume, because air is naturally forced out of the container by the presence of the non-gas fluid. Hence, the volume restriction 12 enhances the performance and efficiency of known filtration systems by limiting the post-filter container to a restricted maximum volume that is less than the unrestricted maximum volume. Preferably, the restricted maximum volume is less than the unrestricted maximum volume, but greater than the volume of biological fluid "F" to be filtered, which allows all of the filtered biological fluid "F" to be held within the post-filter container 24. Alternatively, the restricted maximum volume may be less than or equal to the volume of biological fluid "F" to be filtered, which further prevents residual gas from aggregating in the post-filter container 24 and may force some biological fluid "F" to remain in another portion of the filtration system 10, such as one or more tubing segments 42 (FIGS. 1A-1D) for testing. Preferably, the volume restriction 12 is stationary or fixed with respect to the post-filter container 24 during the filtration process, i.e., it does not require manipulation to limit the maximum volume of the post-filter container 24.

A method of using a filtration system 10 and volume restriction 12 of the present invention is illustrated in FIGS. 1A-1D. The filtration system 10 conforms generally to the foregoing description, with a pre-filter container 14, a filter inlet flow path 18, a filter 28, a filter outlet flow path 22, a post-filter container 24, and a volume restriction 12. Preferably, the system 10 is sterilized prior to use in a filtration procedure, most preferably during the manufacturing process prior to packaging and transport.

Additional components of the illustrated system 10 include a frangible cannula 44 on the filter inlet flow path 18, a filter line clamp or closure device 46, tubing segments 42 of the filter outlet flow path 22, a bypass line 20 joined to the filter inlet flow path 18 and the filter outlet flow path 22 (by a Y-junction, for example), a bypass line clamp or closure device 48, and a one-way valve 50. The tubing segments 42 may be provided if the filtration system 10 is used to process blood or a blood component. The segments 42 store a quantity of filtered fluid apart from the fluid in the post-filter container 24, which stored fluid is generally used for testing prior to use of the fluid in the post-filter container 24. The structure of the segments 42 may vary, but in one embodiment, the segments 42 comprise two- or three-inch tubing portions that are uniquely labeled for each filtration system 10 to ensure traceability. Each segment is sealable and severable from the remainder of the tubing to allow for testing of fluid "F" contained therein prior to transfusion or other use of the filtered fluid "F" in the post-filter container 24. As for the closure devices 48 and one-way valves 50, they may take any of a number of forms, including a slide clamp or hemostat for the closure device 48 and a check valve or hydrophobic element for the one-way valve 50. The selection of these or other closure and valve elements is well within the capabilities of one having ordinary skill in the art.

In use, the pre-filter container 14 is filled with a biological fluid "F" and suspended at a higher vertical elevation than the filter 28 and the post-filter container 24, as shown in FIG. 1A. The filter line clamp 46 is disengaged from the filter outlet flow path 22 and the cannula 44 is broken (FIG. 1B). The biological fluid "F" flows by gravity through the filter inlet flow path 18 and into the filter 28. The pressure required to pass the biological fluid "F" through the filter 28 is developed by gravity acting on the fluid "F" as it flows downwardly from the pre-filter container 14 positioned a selected height above the filter 28. The bypass line clamp 48 prevents flow of the fluid "F" through the bypass line 20, although the one-way valve 50 or a second break-away cannula (not illustrated) may perform the same function if the system 10 is provided without a bypass line clamp 48. When the fluid "F" has primed the filter 28, the fluid "F" and any air in the filter 28 flows through the filter outlet flow path 22, the tubing segments 42, and into the post-filter container 24. The post-filter container 24 expands as it receives the biological fluid "F" and air from the filter 28, and the pressure therein increases. The volume restriction 12 limits the expansion of the post-filter container 24, which tends to further increase the pressure in the post-filter container 24.

At the same time that the pressure in the post-filter container 24 is increasing, the pressure in the pre-filter container 14 is decreasing—typically to a vacuum state. When the pressure in the post-filter container 24 is sufficiently greater than the pressure in the pre-filter container 14, the flow of biological fluid "F" through the filter 28 will cease with an amount of fluid "F" remaining in the filter 28, and possibly in the pre-filter container 14 or filter inlet flow path 18 as well. Ideally, this point occurs with substantially all of the fluid "F" in the post-filter container 24, so that only a small amount of fluid "F" must be flushed from the filter 28. When filtration so ceases, the filter line clamp 46 may be reengaged with the filter outlet flow path 22 and the bypass line clamp 48, if provided, is opened. The pressure in the post-filter container 24 automatically forces the air held therein through the bypass line 20 and the one-way valve 50, into the pre-filter container 14, as shown in FIG. 1C. If present, a vacuum state in the collapsed pre-filter container 14 also assists in drawing fluid "F" upward through the bypass line 20. Thus, the use of the volume restriction 12 will automatically purge all or the majority of air remaining in the post-filter container 24, thereby eliminating the manual "burping" step of known systems and effectively turning them into automatic "burping" systems.

When the air has been re-circulated to the pre-filter container 14, the bypass line clamp 48 is reengaged to the bypass line 20 and the filter line clamp 46 is opened (FIG. 1D). The accumulation of air in the pre-filter container 14 raises the pressure in the filter inlet flow path 18 above the pressure in the filter outlet flow path 22, which allows the remainder of biological fluid "F" to flow through the filter 28. This filtered biological fluid "F" flows into the post-filter container 24 and some remains in the tubing segments 42 to be tested.

After filtration is complete, the filter outlet flow path 22 and/or the segments 42 may be sealed and severed, and the filtered fluid "F" in the post-filter container 24 may be stored, delivered to a recipient, or otherwise processed. For example, if the fluid "F" is whole blood and the filter 28 is a leukoreduction filter, one common post-filtration process is centrifugation of the post-filter container 24. Depending on the nature of the volume restriction 12, it may be removed from the post-filter container 24 or otherwise be deactivated prior to centrifugation, it may remain with the post-filter container 24 throughout centrifugation, or it may be adapted to disengage from the post-filter container 24 or otherwise deactivate during centrifugation.

The filtration systems 10a-10d of FIGS. 2-5 operate similarly to the foregoing method, with variations depending on the particular components. For example, the embodiment of FIG. 4 may allow for continuous air removal from the post-filter container 24, rather than a single purging step. After the system 10c is hung substantially vertically, as shown, cannulas 44 on the filter inlet flow path 18 and bypass line 20 are broken or otherwise opened and fluid flow through the filter 28 begins. Flow through the bypass line 20 is prevented by a loop portion or the like (not illustrated) above the fluid level in the pre-filter container 14 or a one-way valve 50. When the pressure differential between the post-filter container 24 and the pre-filter container 14 reaches a sufficient level, the air is automatically re-circulated through the bypass line 20 to the pre-filter container 14, which essentially allows for "walkaway" operation of the system 10c after the cannulas 44 are opened. The volume restriction 12 acts to further increase the pressure in the post-filter container 24, which encourages air removal therefrom and increases the efficiency of the system 10c.

Figure 3:
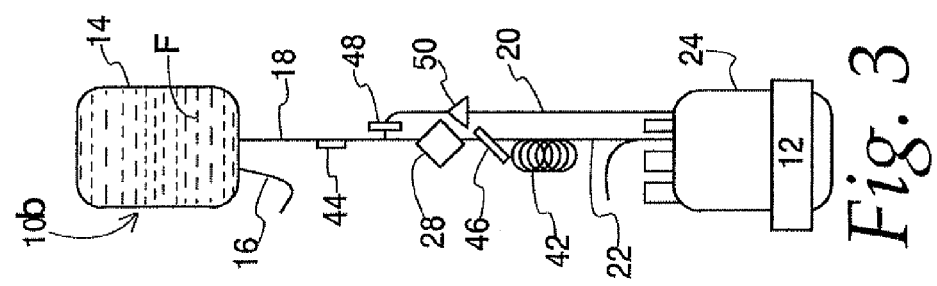
Figure 2:
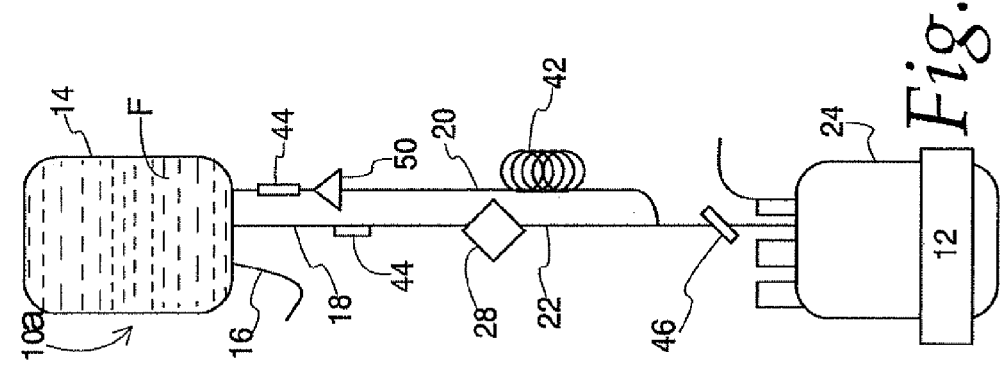

As for the other illustrated systems, the system 10b of FIG. 3 operates generally according to the method shown in FIGS. 1A-1D, with one end of the bypass line 20 being joined directly to the post-filter container 24, instead of to the filter outlet flow path 22. The system 10a of FIG. 2 operates by initially closing flow to the post-filter container 24 with a clamp or closure 46. The cannulas 44 on the filter inlet flow path 18 and the bypass line 20 are opened to allow fluid flow through the filter 28. As the filter 28 primes, the air from the filter 28 is directed through the bypass line 20 and the one-way valve 50, to the pre-filter container 14. If provided on the bypass line 20, the segments 42 will also fill with fluid "F" at this time. To prevent the backflow of fluid "F" into the pre-filter container 14, it may be preferred to provide the one-way valve 50 as a hydrophobic filter. At some point, the backflow of air will cease, at which time the clamp 46 on the filter outlet flow path 22 is opened and filtration will proceed until finished, aided by the air previously circulated to the pre-filter container 14. In this embodiment, the volume restriction 12 aids in removing air from the post-filter container 24 that is initially present as a consequence of the manufacturing process.

Finally, the vented system 10d of FIG. 5 operates according to the foregoing description of U.S. Pat. No. 5,863,436 to Matkovich, although the post-filter vent 52 may be placed in other locations downstream of the filter 28, including on the post-filter container 24. This system 10d is "non-burpable" and not intended for removing air from the post-filter container 24 after the air from the filter is removed through vent 52. Some of the benefits provided by the volume restriction 12 may not be fully realized when used in combination with a "non-burpable" system, so it is preferred to use the volume restriction 12 with "burpable" systems, however the present invention is not so limited and may also be used with "non-burpable" systems, such as the one illustrated in FIG. 5, and other dual-container biological fluid filtration systems not specifically illustrated or described herein.

FIGS. 6A-14 illustrate a variety of volume restrictions according to the present invention. For example, FIGS. 6A-6D show a volume restriction provided as a restrictor member 54. The restrictor member 54 is shown as a belt or band that substantially encircles at least a portion of the post-filter container 24. The post-filter container 24 is expandable from an empty condition (FIGS. 6A and 6C) to a restricted maximum volume (FIGS. 6B and 6D) that is less than the unrestricted maximum volume, which is shown in broken lines in FIGS. 6B and 6D. The restrictor member 54 is substantially non-expandable, or at least less expandable than the post-filter container 24, and acts as an outer boundary for the volumetric expansion of the portion of the container which it surrounds. The placement, size, strength, and inner diameter of the restrictor member 54 determine the restricted maximum volume and may be tailored to the anticipated use of the filtration system. Preferably, the restrictor member 54 is adapted to be used in combination with standard fluid containers, but may also be configured to be used with specially shaped containers.

Numerous variations may be made to the restrictor member 54, such as providing a transparent or semi-transparent restrictor member to allow for improved visibility of the interior of the post-filter container 24. Rather than positioning the restrictor member 54 horizontally, as shown in FIGS. 6A-7D), it may be positioned to vertically or diagonally encircle a portion of the post-filter container 24. The restrictor member 54 may be adapted for tightening or loosening to selectively adjust the inner diameter thereof and, in turn, adjust the restricted maximum volume. If a much smaller restricted maximum volume is desired, a relatively wide restrictor member 54a comprising a sleeve (FIGS. 7A-7D) or a plurality of restrictor members 54 may be used with the post-filter container 24. The restrictor member 54, 54a may be fixedly secured to the post-filter container 24 or removable therefrom. If secured to the post-filter container 24, any of a number of means may be used, including adhesion, welding, crimping, and the like. If removable from the post-filter container 24, the restrictor member 54, 54a may be elastomeric or have a frangible or weakened zone that is broken to disengage the restrictor member. Alternatively, the restrictor member 54, 54a may be adapted to automatically disengage or at least partially separate from the post-filter container 24 when subjected to the pressures of a centrifuge.

FIG. 8A illustrates a volume restriction provided as a cavity-defining housing 56. The housing 56 is more rigid than the post-filter container 24 and defines a cavity 58 adapted to receive at least a portion of the post-filter container 24. The cavity 58 is sized and configured such that it limits the expansion of the container portion received therein to a restricted maximum volume that is less than the unrestricted maximum volume. The magnitude of the restricted volume may be varied by putting a greater or lesser portion of the post-filter container 24 into the cavity 58. The cavity 58 of FIG. 8A has a generally cuboid shape, although other configuration may be used without departing from the scope of the present invention. For example, FIGS. 8B and 8C are cross-sectional views of a housing 56a having a generally "wedge-shaped" cavity 58a, with the perimeter of the cavity 58a decreasing from top to bottom. Such a "wedge-shaped" cavity 58a may be preferred for ease of removing a post-filter container 24 therefrom.

Another variation of the housing is illustrated in FIG. 8D. In this embodiment, the housing 56b includes a second cavity 58', which is adapted to receive a second post-filter container. While the housing 56b is illustrated as having two identical cavities 58 and 58', there may be more than two cavities and/or cavities that are differently shaped, sized, or configured. It will be appreciated that the multiple-cavity housing 56b effectively provides a "volume restriction station" that allows for the simultaneous volume restriction of several post-filter containers, which may be useful for users having a number of filtration applications to carry out.

FIGS. 9A and 9B illustrate an embodiment wherein the volume restriction comprises first and second plates 64. A side view of the plates 64 is shown in FIG. 9B, which shows them as being identical and parallel to each other, but they may be differently shaped and/or divergent without departing from the scope of the present invention. The plates 64 are spaced apart from each other to receive at least a portion of a post-filter container 24 therebetween. While the illustrated plates 64 are larger than the post-filter container 24, one or both of the plates 64 may be smaller than the container 24, such that only a portion of the container 24 is received therebetween. As the post-filter container 24 fills with fluid, it bears against the plates 64 and is prevented from expanding to an unrestricted maximum volume. The plates 64 may be fixedly connected to each other by any of a number of connection means, such as the screws 66 shown in FIGS. 9A and 9B. In one embodiment, the connection means are adapted to allow for selective adjustment of the separation between the plates 64, which the manufacturer or user may adjust to specify the restricted maximum volume.

Figure 10A:
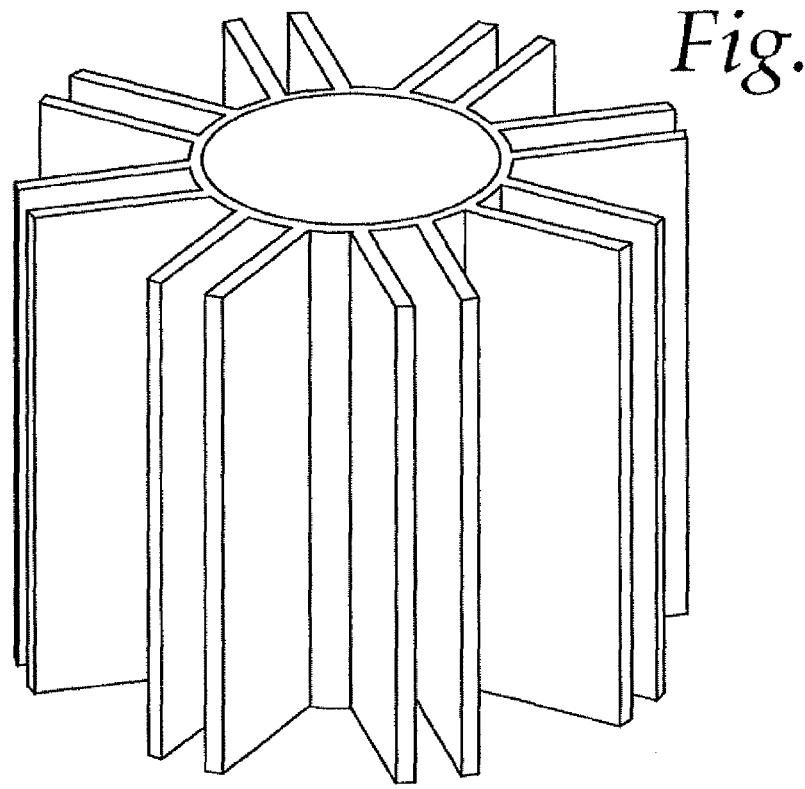
FIG. 10A is a front perspective view of a volume restriction provided as a member having a plurality of external radial slots.
Figure 10B:
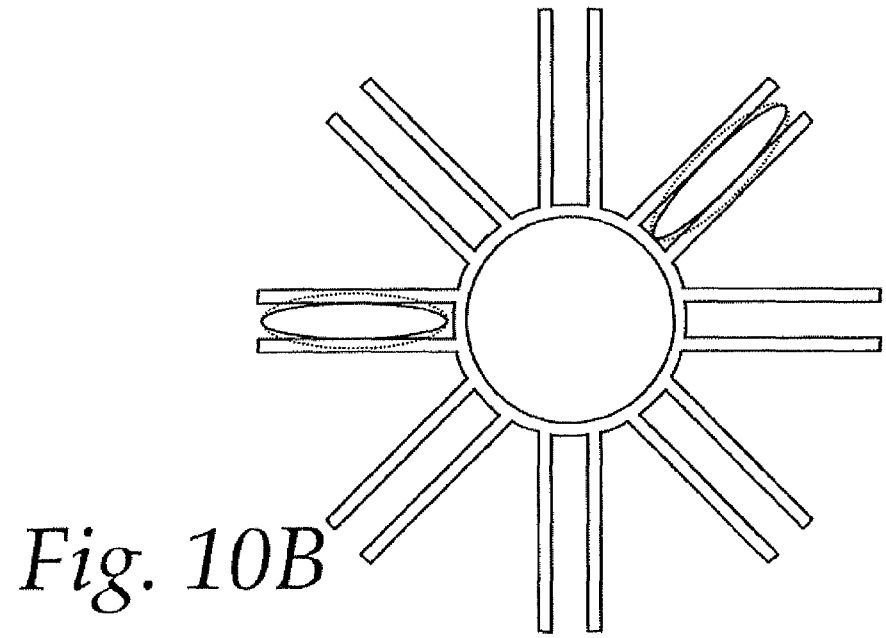
FIG. 10B is a top plan view of the member of FIG. 10A, with a plurality of post-filter containers received by the slots.

Additional plates may be connected to the first and/or second plates 64 to allow for the simultaneous volume restriction of a plurality of post-filter containers, similar to the "volume restriction station" illustrated in FIG. 8D. Another variation of a "volume restriction station" is illustrated in FIGS. 10A and 10B. In this embodiment, the volume restriction comprises a body member 60 having a plurality of plates 64 extending away from the outer surface of the body member 64. The body member 64 is illustrated as a tubular member with radially extending plates 64, but it may be provided in any of a variety of shapes. Adjacent plates define a slot 62 therebetween, which is adapted to receive at least a portion of a post-filter container 24. The shape and size of the slots 62 in the illustrated embodiment depend on the angular separation between adjacent plates and the orientation of adjacent plates (e.g., projecting radially away from the central axis of the body member 60 to form a "wedge-shaped" slot or being parallel to each other, as shown). The illustrated slots 62 are substantially linear and vertical, with a generally uniform width (angular extent) from top to bottom, which maintains a post-filter container 24 received therein in a vertical orientation. However, each slot 62 may be non-linear (e.g., having sinusoidal shapes) and/or non-vertical and may have a varying width along its length. The size and configuration of each slot 62 is sufficiently small to prevent full expansion of the container portion received therein, which limits the container 24 to a restricted maximum volume (FIG. 10B) that is less than the unrestricted maximum volume (shown in broken lines in FIG. 10B).

The volume restrictions of FIGS. 8A-10B may be adapted to rest on the ground or other surface or to be suspended above the ground with the post-filter container 24. Preferably, these volume restrictions are adapted to be used in combination with standard fluid containers, but they may also be configured to be used with specially shaped containers. Further, although the housings and plates are illustrated as being solid, they need not be solid and may take a variety of forms, such as mesh-like or other.

Figure 11A:
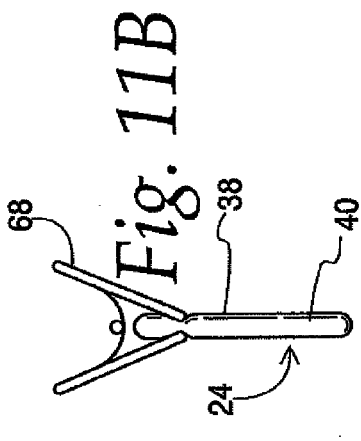
FIG. 11A is a front elevational view of a post-filter container having a volume restriction provided as an external clamp.
Figure 11B:
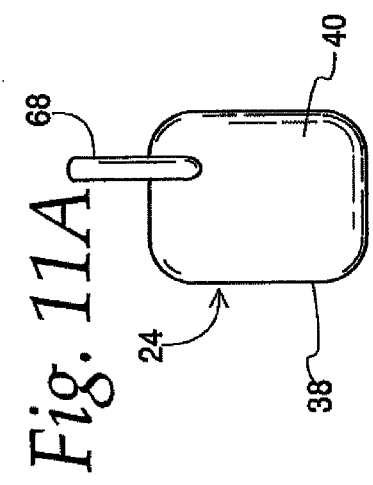
FIG. 11B is a side elevational view of the post-filter container and clamp of FIG. 11A.

FIGS. 11A and 11B illustrate an embodiment of the volume restriction as an external clamp of clip 68. The clamp 68 is illustrated as a typical spring clamp or squeeze clamp, but any squeezing or pinching means (including a one-piece, slide-on "paperclip-like" clip) may also be used without departing from the scope of the present invention. The clamp 68 engages the sidewall 38 of the post-filter container 24 and presses opposing portions of the sidewall 38 against each other in the container interior 40. By action of the clamp 68, the available volume within the interior 40 effectively decreases, as fluid cannot occupy the space between the opposing sidewall portions. Further, it will be appreciated that the clamp 68 prevents or at least limits expansion at and adjacent to the opposing sidewall portions by pressing the opposing portions together. The clamp 68 may be removable from the post-filter container 24, allowing repositioning prior to filtration and/or removal after filtration. Alternatively, a non-removable clamp or a plurality of removable/non-removable clamps may also be used without departing from the scope of the present invention.

Figure 12A:
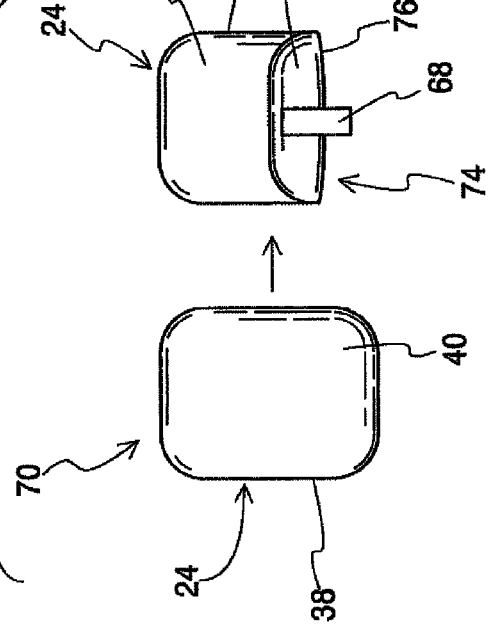
FIG. 12A is a front elevational view of a post-filter container in an original condition and a deformed condition.
Figure 12B:
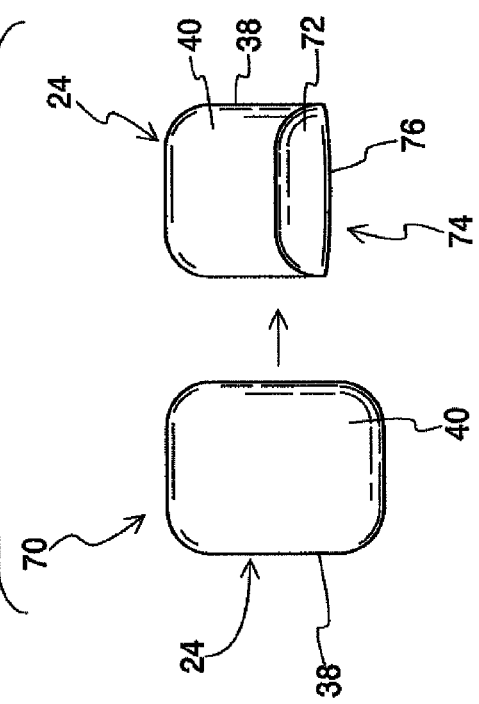
FIG. 12B is a front elevational view of the post-filter container of FIG. 12A, with the deformed condition maintained by an external clamp.

FIGS. 12A and 12B illustrate an embodiment wherein the volume restriction comprises a deformation of the post-filter container 24. As shown in FIG. 12A, the post-filter container 24 is initially provided in an original condition 70, which is typically substantially flat. A deformed portion 72 is created by deforming the post-filter container 24 from the original condition 70 to a deformed condition 74. The deformed portion 72 of FIG. 12A is formed by creasing and folding a bottom section of the post-filter container 24, so it is referred to herein as a "folded portion," although other deformations, such as tightly rolling a portion of the container, are possible and within the scope of the present invention. The folded portion 72 is separated from the remainder of the container interior by a crease 76, which preferably prevents the inflow of biological fluid into the folded portion 72 during filtration. Hence, it will be appreciated that the available interior volume of the post-filter container 24 is decreased by an amount substantially equal to the volume of the folded portion 72. Similarly, the maximum expanded volume is decreased from an unrestricted maximum expanded volume to a restricted maximum expanded volume, which achieves the benefits previously described herein.

Preferably, the integrity of the folded portion 72 is maintained throughout the filtration process, such that fluid is not allowed into the folded portion 72 during filtration. For example, as shown in FIG. 12B, the folded portion 72 may be enforced by a clamp or clip 68 similar to that illustrated in FIGS. 11A and 11B. In another embodiment, the folded portion 72 is adhered or otherwise bonded to the remainder of the post-filter container 24 to prevent a return to the original condition 70 during filtration.

FIGS. 13A-14 illustrate embodiments wherein the volume restriction is provided as a bond 78 in the interior 40 of the post-filter container 24. As per the foregoing description, the post-filter container 24 may be comprised of, inter alia, a sidewall 38 that defines an open interior portion 40. In the embodiments of FIGS. 13A-14, opposing portions of the sidewall 38 are bonded together in the interior portion 40, which limits the interior volume and the maximum expanded volume. The bond 78 may be provided as a surface bond, achieved by an adhesive or surface finish or the like, or a structural bond, achieved by melt-bonding or the like. For example, in one embodiment, opposing portions of the sidewall 38 are treated with a surface finish (such as a heat-activated adhesive) that is adapted to bond the opposing portions together when the post-filter container 24 is sterilized prior to use. Of course, the nature of the bond is dependent on the material of the sidewall 38 and will vary accordingly, so this aspect of the present invention is not limited to a particular bonding process or configuration.

Although the bond 78 is described as being in the interior portion 40 of the post-filter container 24, this aspect of the present invention is not limited to a manufacturing step taking place within the interior portion 40, such as the application of adhesive to the sidewall 38. On the contrary, this aspect of the present invention may include external manipulation that results in a bond 78 in the interior portion 40, such as a melt-bonding process that involves the application of heat to the outside of the sidewall 38, which is then pressed against an opposing portion thereof to establish a structural bond in the interior portion 40.

FIGS. 13A-13D illustrate various embodiments of a bond 78 occupying a significant section of the interior portion 40, which will significantly decrease the maximum expanded volume, although the bond 78 is not limited to a specific size or shape. Further, it will be seen from FIGS. 13A-13D that the bond 78 may be located in a variety of different positions within the post-filter container 24, but the illustrated configurations are exemplary, rather than limiting, and the bond 78 may be positioned virtually anywhere within the interior portion 40.

FIG. 14 illustrates a plurality of smaller bonds 78 that each joins together highly localized opposing portions of the container sidewall 38. The opposing sections of the sidewall 38 at each bond 78 are held together and at least substantially (if not completely) prevented from expanding upon receipt of a fluid into the post-filter container 24. Similarly, the sections of the container sidewall 38 adjacent to each bond 78 are pulled toward each other, which limits their ability to expand upon receipt of a fluid into the post-filter container 24.

Preferably, the bonds 78 are sufficiently strong that they will not release during filtration. In one embodiment, the bonds are frangible at a force greater than the forces typically present during filtration, which allows at least partial separation of the opposing sidewall portions from each other. For example, a bond may be partially or completely broken to increase the maximum expanded volume before, during, or after filtration. Such a feature may be useful in providing a post-filter container with a relatively large bond that is partially broken by a user prior to filtration according to the amount of fluid to be processed. If the bond is adapted to be broken before or during filtration, it is preferably provided by a bio-compatible adhesive material that will not contaminate the fluid upon contact therewith.

Figure 15:
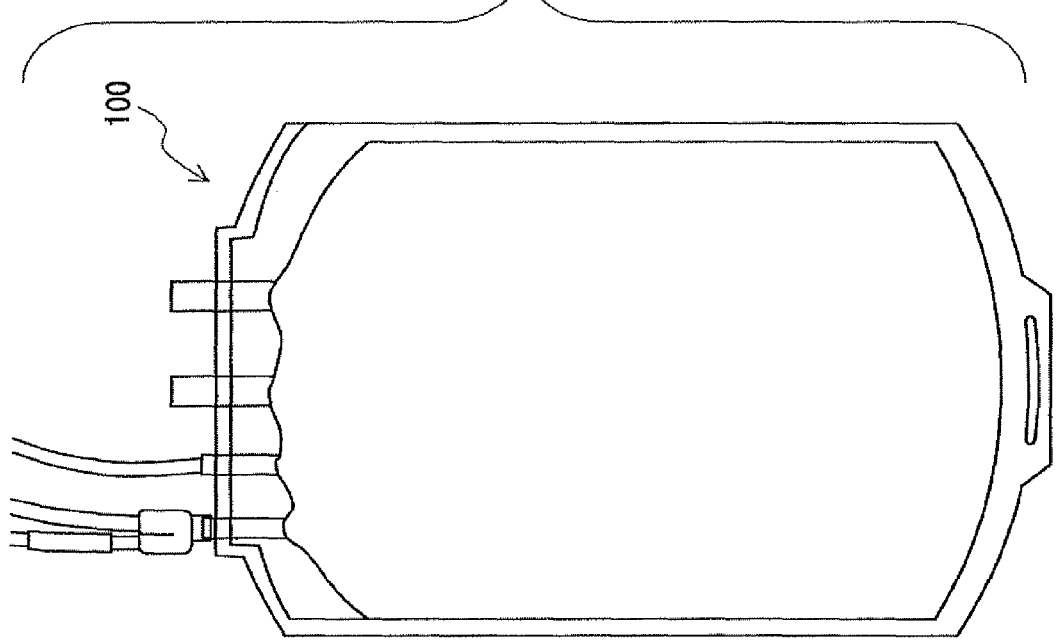
FIG. 15 is a front elevational view of a post-filter container according to an aspect of the present invention and a known post-filter container.

Rather than providing a separate volume restriction element or modifying a known post-filter container to limit its expansion during filtration, a filtration system may be provided with a post-filter container having a relatively smaller maximum volume. For example, FIG. 15 shows the difference between a known post-filter container 100 and an exemplary post-filter container 102 having a relatively smaller maximum volume according to an aspect of the present invention.

In the United States, it is common to perform leukoreduction on an approximately 500 ml volume of whole blood, which volume may range from approximately 400-550 ml. The unfiltered whole blood is first collected in a pre-filter container, conforming generally to the foregoing description, which may contain approximately 63-70 ml of anticoagulant. Hence, the combined volume of fluid in the pre-filter container is approximately 463-620 ml. In contrast, for a typical red blood cell leukoreduction operation, 200-350 ml of separated red blood cells including 90-110 ml of additive solution may be provided in the pre-filter container for filtration. The foregoing are merely exemplary and other volumes and biological fluids may also be used in combination with systems and methods according to the present disclosure.

Using known leukoreduction filters and filtration methods with anticoagulated whole blood, it has been found that approximately 5-15% of the volume filtered is ultimately retained in the filter. The amount of fluid retained in the filter during the filtration process is referred to herein as the "retention volume" and may depend on a number of factors, including the nature of the filter material, the size or volume of the filter housing, the nature of the biological fluid, and the pressure of the fluid as it enters the filter (corresponding to the height at which the pre-filter container is hung above the filter). The retention volume may be decreased by venting gas from the post-filter container to the pre-filter container or the filter inlet flow path after flow through the filter initially stops, in accordance with the foregoing description. Moving or venting this gas to a location within the system above the filter increases the pressure on any unfiltered biological fluid, forcing more of the fluid through the filter and into the post-filter container, thereby decreasing the retention volume of the filter.

After accounting for the amount of the original 463-620 ml of biological fluid ultimately retained by the filter (i.e., the retention volume), the post-filter container may receive approximately 394-589 ml of filtered fluid. The quantity of biological fluid that is actually filtered and passed into the post-filter container is referred to herein as the "filtered fluid volume."

In addition to the filtered fluid, the post-filter container will also receive any gas resident in the filtration system. For example, in known systems there may be approximately 90-ml of air in the system, with approximately 40-60 ml of this air in the filter and the remainder in the post-filter container and/or the tubing. Ultimately, the total volume received by the post-filter container (including gas) may be approximately 434-649 ml, most typically around 535 ml.

Known post-filter containers have a maximum volume that is substantially greater than necessary to hold the filtered fluid volume. For example, known post-filter containers, such as the container 100 of FIG. 15, may have a size of about 5 inches×7 inches for a container formed by peripherally sealing facing layers of polyvinyl chloride (PVC) film. This translates to a maximum vented volume of at least approximately 635 ml, which is too large to create an internal pressure sufficiently great to exit gas in an automatic venting feature, and the container 100 must be squeezed to remove gas. When used herein, the term "maximum vented volume" refers to the effective volume of a post-filter container having an associated bypass line or other suitable gas vent passageway or mechanism. The absolute maximum volume of such known containers (i.e., the maximum volume in the absence of a venting mechanism) may be approximately 822.67 ml, whereas the associated bypass line allows for nominal gas release from the container during filtration and a "maximum vented volume" of at least approximately 635 ml.

In one embodiment of this aspect of the present invention, the post-filter container has a maximum volume able to contain at most the combined volume of filtered fluid and air when fully filled and distended under pressure of the filtration fluid head. This leads to an increased internal pressure during filtration and results in automatic gas venting from the container. In an exemplary embodiment illustrated in FIG. 15, a post-filter container 102 according to this aspect of the present invention, as adapted for use in a filtration operation according to the foregoing description, may have a size that is about 6 inches×5.25-5.3 inches, which is a material requirement about 9.1% less than the known container 100. Such a smaller container 102 may have a maximum vented volume of approximately 535 ml or a maximum vented volume in the range of approximately 535-555 ml, which is sufficiently large to receive all of the filtered fluid, while also being sufficiently small to automatically exit all or at least a substantial portion of the air received therein during filtration. A container according to this exemplary embodiment may have an absolute maximum volume of approximately 656.70 ml, compared to the absolute maximum volume of approximately 822.67 ml for known containers.

While a post-filter container sized and configured according to the foregoing description may be preferred for the described filtration operation, this aspect of the present invention is not limited to filtration of a particular fluid or a post-filter container with a particular maximum volume, as the container maximum vented volume is preferably selected to account for a number of factors, such as the fluid volume to be filtered, the retention volume of the filter, the height at which the pre-filter container is hung above the filter (i.e., the pressure of the biological fluid as it enters the filter), the estimated air or gas resident in the filter, the configuration of the filtration system (e.g., whether gas vented from the post-filter container is used to push additional biological fluid through the filter), and the particular filtration method employed. Accordingly, while the specific examples of volume and size may be suitable for the illustrated system, the volume or size of the smaller container will vary according to various factors such as described above. For example, in other embodiments, the post-filter container may be approximately 4⅞ inches wide×6.5 inches long or approximately 4.75 inches wide×7 inches long or 4⅞ inches wide×5⅜ inches long.

In another embodiment, the filtered fluid volume is calculated (taking into consideration, for example, the aforementioned factors) and the post-filter container is configured to have a maximum vented volume approximately the same as the filtered fluid volume, such that there is ideally relatively little or no gas remaining in the post-filter container following the filtration process. For purpose of this description, "approximately the same" means up to ±19% or, more preferably a narrower range of ±4%, as explained in more detail below. To optimize the performance of the system, it may be provided with instructions to the end user indicating, for example, the nature and amount of biological fluid to be filtered, the height above the filter at which the pre-filter container is to be hung, and the steps to carry out in filtering the biological fluid. To more closely control the height at which the pre-filter container is hung above the filter, the system may be provided with a fixture configured to secure the various components of the system at the proper height and in the correct alignment.

To account for variables in the filtration process, the post-filter container may be configured to have a maximum vented volume that is slightly greater or less than the estimated quantity of filtered biological fluid that will ultimately be passed thereinto. For example, the post-filter container may be provided with a maximum vented volume that is no more than approximately 19% greater or less than the quantity of filtered biological fluid that is expected to be passed thereinto. In another embodiment, the post-filter container may be provided with a maximum vented volume that is no more than approximately 20 ml greater or less than the quantity of filtered biological fluid that is expected to be passed thereinto. More preferably, the post-filter container has a maximum vented volume that is no more than approximately 4% greater or less than the quantity of filtered biological fluid that is expected to be passed thereinto. Providing a post-filter container smaller than the calculated filtered fluid volume may be advantageous when gas removal is prioritized by the end user or when some of the filtered fluid is maintained elsewhere (e.g., in tubing segments). On the other hand, providing a post-filter container larger than the calculated filtered fluid volume may be advantageous when the volume of collected fluid is prioritized over more complete gas removal by the end user or when emphasis is placed on decreasing the filtration time.

In general, the post-filter container preferably is sized and has a shape and elastic properties such that, when filled, it has created an internal pressure sufficient to automatically exit all or at least a substantial portion of the air within through a venting or bypass means (such as a bypass line according to the foregoing description). A number of other objectives may also be accounted for in designing a post-filter container according to this aspect of the present invention. Those considerations include providing a post-filter container that will operate to automatically vent gas without significantly impacting the time required to fill the container. In some operations, such as filtering whole blood, the filtered fluid in the post-filter container is centrifuged, so another consideration is providing a smaller post-filter container that will be compatible with existing centrifuge buckets, such that the container will fit in commercially available centrifuge buckets as well as conforming to their geometry to avoid breaking under centrifugation pressures. Yet another consideration is the fact that, if the post-filter container is formed from a PVC material and steam sterilized, it will shrink during manufacture, so the dimensions of the sheeting material must be selected to account for any shrinkage or other dimensional variation arising during or after the manufacturing process.

As referred to above, in one exemplary embodiment illustrated in FIG. 15, a post-filter container 102 for leuko-reducing whole blood is approximately 6 inches long and approximately 5.25-5.3 inches wide (before sterilization) and has a maximum vented volume of approximately 535 ml or a maximum vented volume in the range of approximately 535-555 ml. This is in contrast to, for example, a current whole blood post-filter container from Fenwal Inc., which is approximately 7 inches long and approximately 5 inches wide (before sterilization) and has a maximum vented volume of at least approximately 635 ml. A post-filter container 102 according to this exemplary embodiment may be constructed from known materials, such as PL146-2 sheeting with a 0.0145 inch nominal thickness from Baxter International Inc. A post-filter container so constructed has been found to be sufficiently large to hold all of the filtered fluid in a typical whole blood filtration operation, while being sufficiently small to automatically vent all or substantially all of the gas moved into the container during filtration. Further, such a container is suitable for use with existing centrifuge buckets and provides all of these benefits without significantly impacting the time required to fill the container.

While decreasing the height and/or width of the container is one approach to minimizing the maximum vented volume, other approaches are also possible. For example, the maximum vented volume may be made relatively smaller by increasing the thickness and/or rigidity of the sheeting material, thereby limiting the expandability of the container and increasing the pressure developed within the container during filtration, which increases gas removal, effectively decreasing the maximum vented volume. It will be appreciated that a number of factors affect the maximum vented volume of the post-filter container, including but not limited to the height, width, sheet rigidity, and seal arrangement and any one or more of these factors may be modified to achieve a relatively smaller maximum vented volume. Thus, this aspect of the present invention is not limited to the modification of any particular aspect of the post-filter container and broadly includes any modification to the container directed to providing a relatively smaller maximum vented volume.

Fluid filtration using post-filter containers according to this aspect of the present invention may be accomplished using any of the systems generally illustrated in FIGS. 1A-5 or any other filtration system involving the transfer of fluid from a source (typically a pre-filter container), through a fluid conduit having a filter or fluid treatment device, to a post-filter container. It may be preferred to provide a system with a vent or bypass line in fluid communication with the post-filter container to improve automatic gas removal during filtration.

A wide variety of biological fluid filtration methods using a pre-filter container, a filter or fluid treatment device, and a post-filter container are well-known to those of ordinary skill in the art and may be practiced with a post-filter container according to this aspect of the present invention.

It will be understood that the embodiments described above are illustrative of some of the applications of the principles of the present invention. Numerous modifications may be made by those skilled in the art without departing from the spirit and scope of the invention, including those combinations of features that are individually disclosed or claimed herein. For these reasons, the scope of the invention is not limited to the above description but is as set forth in the following claims.

The invention claimed is:

1. A method of filtering leukocytes from a quantity of biological fluid, comprising:

flowing a quantity of biological fluid under the force of gravity through a leukocyte removal filter and into a post-filter container, wherein the post-filter container has a maximum vented volume that is approximately the same as the quantity of biological fluid flowed through the filter and into the post-filter container; and venting at least a substantial portion of any gas therein from the post-filter container without separately restricting expansion of the post-filter container and without manually manipulating the post-filter container to expel gas.

2. The method of claim 1, wherein the maximum vented volume of the post-filter container is no more than approximately 19% greater or less than the quantity of biological fluid flowed through the filter.

3. The method of claim 1, wherein the maximum vented volume of the post-filter container is no more than approximately 20 ml greater or less than the quantity of biological fluid flowed through the filter.

4. The method of claim 1, wherein the filter and the post-filter container comprise a closed fluid flow system.

5. The method of claim 1, wherein the filter has a retention volume corresponding to the amount of biological fluid retained by the filter during gravity filtration of the biological fluid, and wherein the maximum vented volume of the post-filter container is based at least in part on the retention volume.

6. The method of claim 1, wherein said flowing a quantity of biological fluid under the force of gravity through a leukocyte removal filter and into a post-filter container includes flowing the quantity of biological fluid from a selected height above the filter, and wherein the maximum vented volume of the post-filter container is based at least in part on said height.

7. The method of claim 1, wherein said biological fluid includes whole blood.

8. The method of claim 1, wherein said biological fluid includes a separated blood component.

* * * * *